US011766204B2

(12) United States Patent
Burton et al.

(10) Patent No.: US 11,766,204 B2
(45) Date of Patent: Sep. 26, 2023

(54) MULTI-SENSOR MAGNETO-MONITORING-IMAGING SYSTEM

(71) Applicant: The Korea Research Institute of Standards and Science ("KRISS"), Daejeon (KR)

(72) Inventors: David Burton, Abbotsford (AU); Kwon Kyu Yu, Daejeon (KR); Yong-Ho Lee, Daejeon (KR); Hyuk Chan Kwon, Daejeon (KR); Jin Mok Kim, Daejeon (KR); Sang Kil Lee, Daejeon (KR)

(73) Assignee: The Korea Research Institute of Standards and Science ("KRISS"), Daejeon (KR)

( * ) Notice: Subject to any disclaimer, the term of this patent is extended or adjusted under 35 U.S.C. 154(b) by 609 days.

(21) Appl. No.: 16/608,843

(22) PCT Filed: May 4, 2018

(86) PCT No.: PCT/IB2018/053101
§ 371 (c)(1),
(2) Date: Oct. 27, 2019

(87) PCT Pub. No.: WO2018/207061
PCT Pub. Date: Nov. 15, 2018

(65) Prior Publication Data
US 2020/0196887 A1  Jun. 25, 2020

(30) Foreign Application Priority Data
May 12, 2017  (AU) ............................... 2017901777

(51) Int. Cl.
*A61B 5/245*   (2021.01)
*A61B 5/00*    (2006.01)
(Continued)

(52) U.S. Cl.
CPC ............ *A61B 5/245* (2021.01); *A61B 5/0042* (2013.01); *A61B 5/243* (2021.01); *A61B 5/369* (2021.01);
(Continued)

(58) Field of Classification Search
CPC .................... G01R 33/0358; A61B 2562/0223
See application file for complete search history.

(56) References Cited

U.S. PATENT DOCUMENTS 5,713,354 A * 2/1998 Warden ................. A61B 5/245
                                                          600/409
5,880,588 A    3/1999 Kado
(Continued)

FOREIGN PATENT DOCUMENTS

DE      10234676 A1 *  2/2004   ......... A61B 5/04008
EP       1049402 B1 * 11/2001   ......... A61B 5/04005
(Continued)

OTHER PUBLICATIONS

Lee et al., A whole-head magnetoencephalography system with compact axial gradiometer structure, 2009 Supercond. Sci. Technol. 22 045023, hereafter Lee (Year: 2009).*
(Continued)

*Primary Examiner* — John Denny Li (57) ABSTRACT

The present invention provides a magnetic monitoring system for imaging, monitoring, scanning or mapping for brain or heart activity of subjects including children and adults, the system comprising of a magnetoencephalographic or magnetocardiographic system incorporating SQUID sensors for measuring brain activity or heart activity, the system including a plurality of Dewar helmets of variable sizes and shapes; and a plurality of monitoring interfaces; wherein the sensor system helmet is moveable by horizontal Dewar rotation. The sensor system includes configurations where
(Continued)

Example of preferred embodiment of MMS OrionLifeSpan Multi-Sensor System (in this MEG example multi- helmet) system the size and shape of helmets in the system may be different to accommodate different sized subjects for monitoring simultaneously.

13 Claims, 7 Drawing Sheets

(51) Int. Cl.
*G01R 33/035* (2006.01)
*A61B 5/243* (2021.01)
*A61B 5/369* (2021.01)

(52) U.S. Cl.
CPC .......... *A61B 5/4064* (2013.01); *A61B 5/6803* (2013.01); *A61B 5/6814* (2013.01); *G01R 33/0358* (2013.01); *A61B 2562/0223* (2013.01)

(56) References Cited

U.S. PATENT DOCUMENTS

| | | | | |
|---|---|---|---|---|
| 6,602,227 | B1* | 8/2003 | Cimino | A61F 9/00745 604/113 |
| 6,628,978 | B1 | 9/2003 | Kondo et al. | |
| 2006/0020165 | A1* | 1/2006 | Adams | A61B 1/00142 600/157 |
| 2006/0122496 | A1* | 6/2006 | George | G01R 33/285 600/424 |
| 2008/0084204 | A1 | 4/2008 | Seki | |
| 2008/0192459 | A1* | 8/2008 | Kwok | F21V 23/04 362/253 |
| 2015/0057550 | A1* | 2/2015 | Kim | A61B 34/30 901/47 |
| 2016/0136308 | A1* | 5/2016 | Flynn | A61B 5/415 424/9.34 |

FOREIGN PATENT DOCUMENTS

| | | | |
|---|---|---|---|
| JP | 04-109930 | 4/1992 | |
| JP | 08-126624 | 5/1996 | |
| JP | 08-181807 | 7/1996 | |
| JP | 2002-336211 | 11/2002 | |
| WO | WO 99/37206 | 7/1999 | |
| WO | 2013/026749 | 2/2013 | |
| WO | WO 2013/026749 | 2/2013 | |
| WO | WO-2013026749 A1 * | 2/2013 | ......... A61B 5/04008 |
| WO | WO 2017/017444 | 2/2017 | |

OTHER PUBLICATIONS

Roberts et al., Artemis 123: development of a whole-head infant and young child MEG system, Front Hum Neurosci. 2014; 8: 99. Published online Mar. 3, 2014. doi: 10.3389/fnhum.2014.00099, hereafter Roberts (Year: 2014).*
Machine Translation of DE10234676 (Year: 2004).*
ISR, dated Aug. 3, 2018.
Written Opinion of International Searching Authority, dated Aug. 3, 2018.
Lee, Y. H. et al., A whole-head magnetoencephalography system with compact axial gradiometer structure, Superconductor Science and Technology, vol. 22, No. 4, pp. 1-6, Mar. 17, 2009.
Roberts, T. P. L. et al., Artemis 123: development of a whole-head infant and young child MEG system, Frontiers in Human Neuroscience, vol. 8, Article 99, pp. 1-10, Mar. 3, 2014.
Notice of Reasons for Rejection dated Nov. 10, 2020 From the Japan Patent Office Re. Application No. 2019-559075. (5 Pages).
Lee et al. "A Whole-Head Magnetoencephalography System With Compact Axial Gradiometer Structure", Superconductor Science and Technology, 22(4): 045023-1-045023-6, Mar. 17, 2009.
Examination Report Under Sections 12 & 13 of the Patents Act, 1970 and the Patents Rules, 2003 dated Feb. 28, 2022 From the Government of India, Intellectual Property India, Patents, Designs, Trade Marks, Geographical Indications, The Patent Office Re. Application No. 201917041214. (6 Pages).

* cited by examiner

Figure 1 Example of preferred embodiment of MMS OrionLifeSpan Multi-Sensor System (in this MEG example multi- helmet) system Figure 2 Example embodiment of exploded diagrammatic views of present invention showing dual-helmet dewer configuration with horizontal rotation ((1) and vertical angular tilt adjustment capabilities (2)

Figure 3 Exploded diagrammatic views showing an example of the dual-dewar function, incorporating vertical height adjustment capability (1), enabling accommodation or different bed, seat, standing or other subject variable imaging and/or monitoring requirements.

Figure 4 Example of magnetic shielded room (2) and reliquifier coolant system (1).

Figure 5 Example of schematic plan of dual-helmet selectable dewar system (5) to accommodate child (3) or adult (4) child inside shielded room (1) with external and adjacent computer processing room (2).

Figure 6 Example of exploded diagrammatic view of dual-helmet dewar system adjusted for 45 degree tilted angle (1) position to accommodate child helmet (2) and associated child subject in seated position (2).

Figure 7 Example of dual-helmet dewar system adjusted for horizontal or non-tilted position (1) to accommodate adult shaped and sized helmet (3) with associated sensor system for imaging and monitoring adult subject lying in supine position (2).

Figure 8 Example of dual-helmet dewar system adjusted for horizontal or non-tilted position (1) to accommodate child shaped and sized helmet (2) with associated sensor system for imaging and monitoring child subject lying in supine position (3).

Figure 9 Example embodiment of MMS with dual-sensor/helmet dewar system.

Figure 10 Example of image and monitoring neural source localisation and image reconstruction conducted in adjoining computer processing room.

MULTI-SENSOR MAGNETO-MONITORING-IMAGING SYSTEM

FIELD OF INVENTION

The present invention relates to bio imaging and bio-monitoring, in particular, radiofrequency beam forming and targeting for treatments.

PRIOR ART OF INVENTION AND LIMITATIONS

A number of magnetoencapholography (MEG) manufacturers have produced varying types of MEG systems. Prior art MEG manufacturers have presented systems capable of enabling their MEG helmet and associated Dewar vessels for containing liquid nitrogen to be adjusted for different subject positions during the MEG brain scanning process. In this way, the prior art MEG systems can be adjusted to accommodate various subject positions during MEG scanning, including seated, supine (such as lying in a bed), as well as other subject positions and different heights. For example, Elekta (a Swedish MEG manufacturer) presented an MEG scanner capable of enabling the MEG Dewar and helmet to be tilted in a manner whereby the subject can undergo MEG brain scanning whilst positioned on a bed in supine position or whilst seated in an upright position. In another example, the Korean Research Institute of Standards and Science (KRISS) presented an MEG scanner capable of enabling the MEG Dewar and helmet which could be lowered and lifted in order to be adjusted to safely and effectively accommodate the different heights of seated subject.

Some of the shortcomings or the prior art include that current Multi-Sensor Magneto-Monitoring-Imaging System (MMS, including MEG, MCG and subject or object magneto monitoring and imaging systems) have limited capability to accurately image and/or monitor MMS/MEG signals because Dewars known in the art are spatially limited in movement and positioning capabilities, thus restricting the morphological characteristics (i.e. ability to reconstruct a realistic or accurate spatial sources, connectivity and connectivity of brain signals) of subjects monitored from brain activity.

SUMMARY OF THE INVENTION

Figure 1:
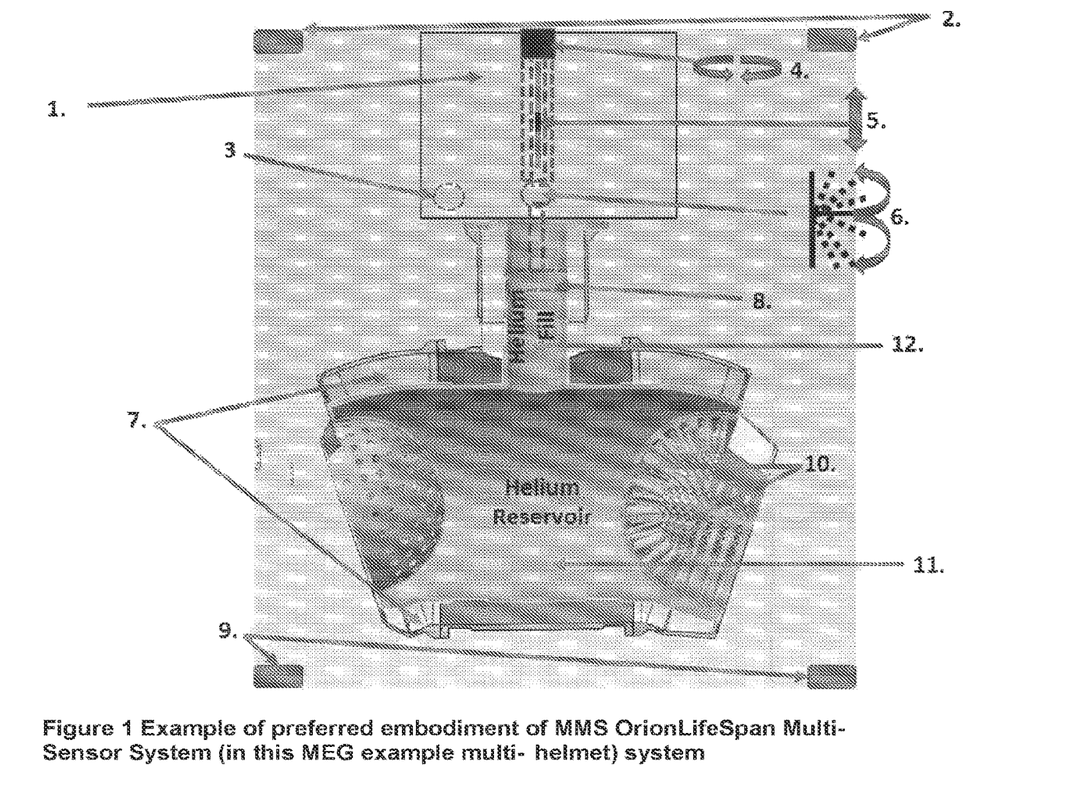
FIG. 1 shows an example of preferred embodiment of MMS OrionLifeSpan Multi-Sensor System (in this MEG example multi-helmet) system
Figure 6:
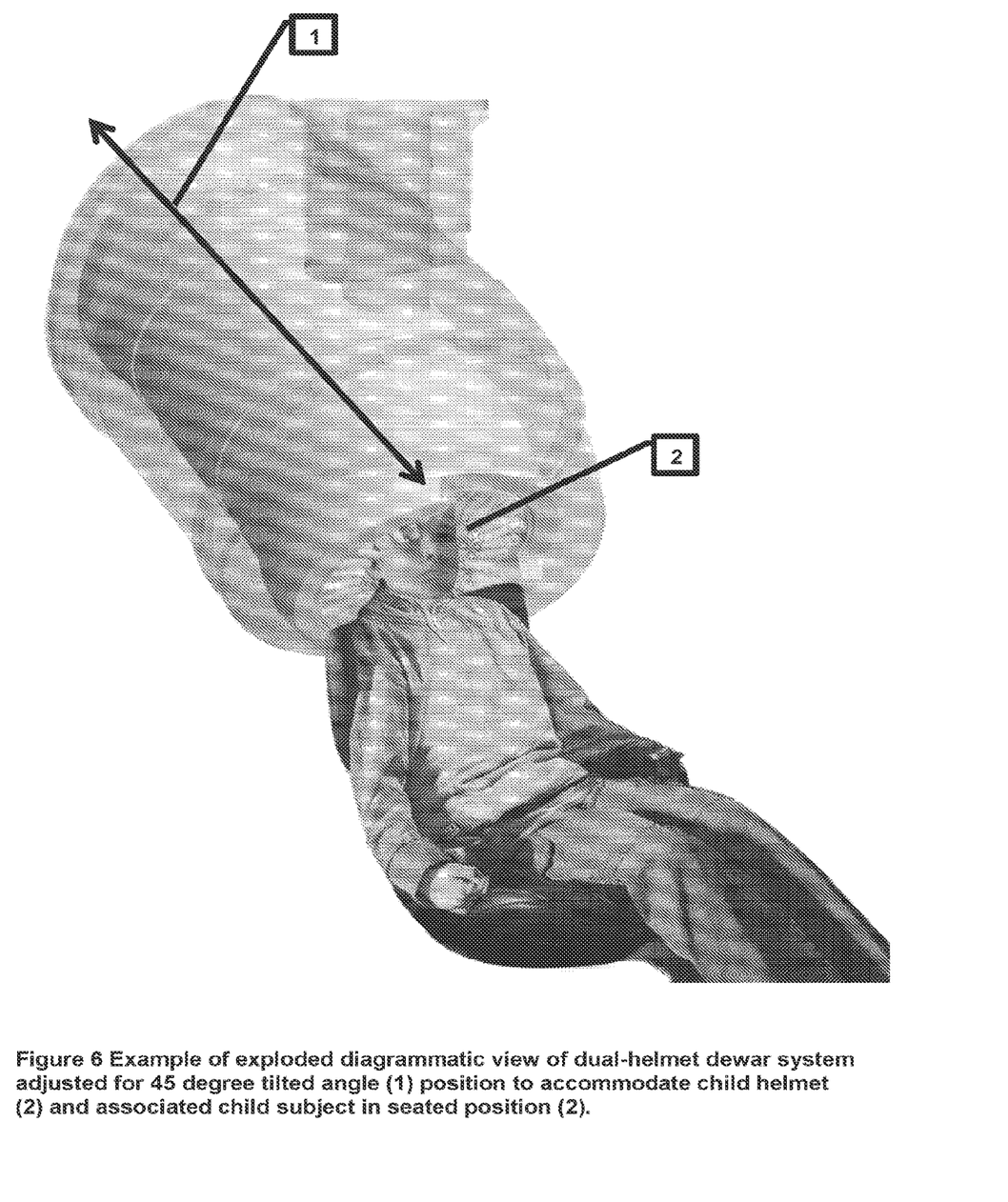
FIG. 6 shows an exploded diagrammatic view of a dual-helmet Dewar system adjusted for 45 degree tilted angle position to accommodate child helmet (2) and associated child subject in seated position
Figure 7:
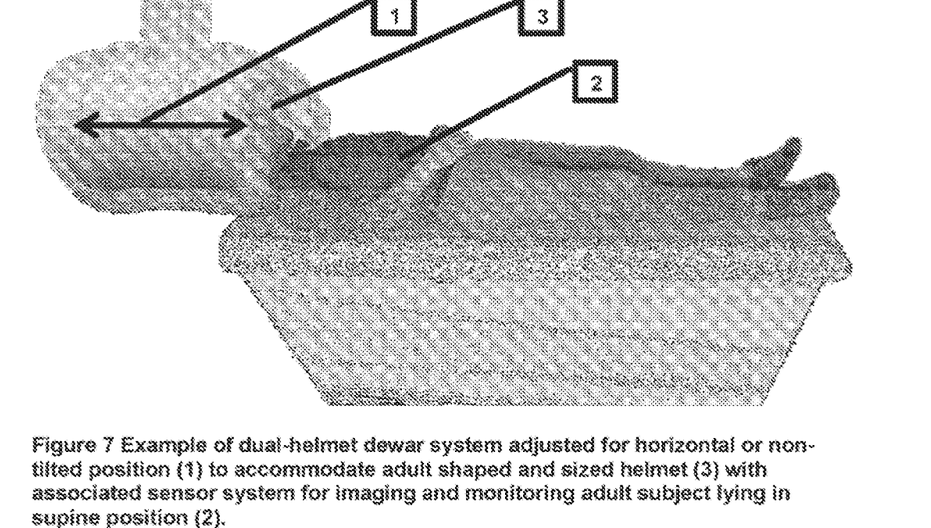
FIG. 7 shows an example of a dual-helmet Dewar system adjusted for horizontal or non-tilted position (1) to accommodate adult shaped and sized helmet with associated sensor system for imaging and monitoring adult subject lying in supine position.
Figure 9:
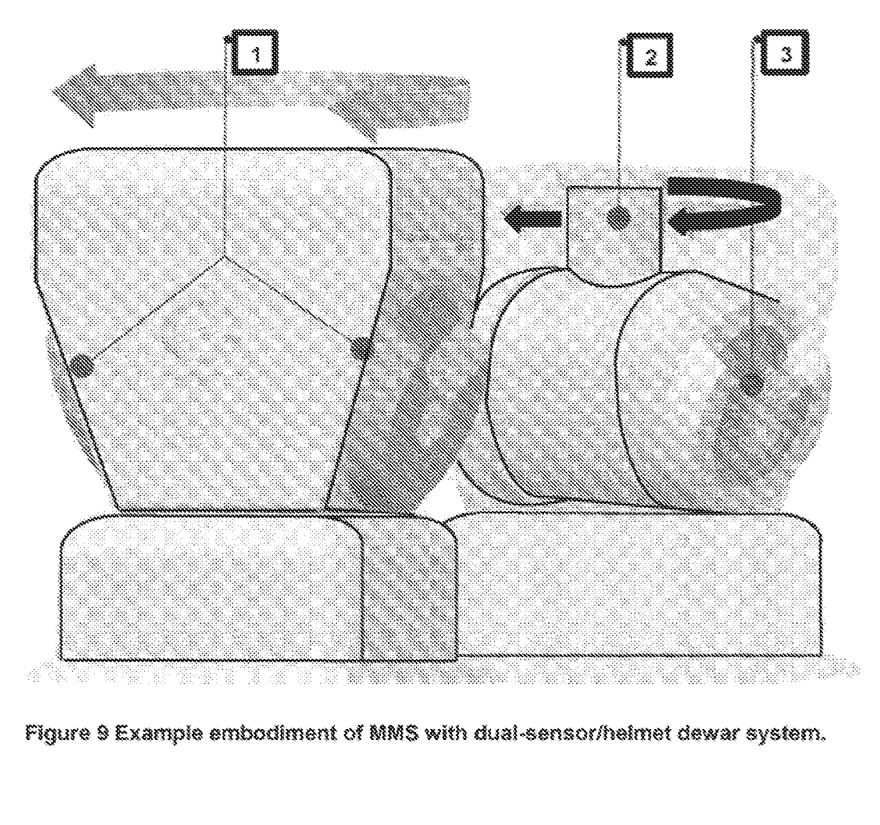
FIG. 9 shows an embodiment of a MMS with dual-sensor/helmet Dewar system.

The present invention comprises of a Magnetic Monitoring System (MMS refers to imaging and/or monitoring and/or scanning and/or mapping system, such as Magnetoencephalography (MEG) and/or Magnetocardiography (MCG)) incorporating a multi-sensor-system (plurality of helmets and/or other Dewar subject imaging or monitoring interfaces, per FIG. 1; FIG. 3, block 5; FIG. 6, block 6; FIG. 7; block 1; FIG. 9, block 1) enabling optimal sensor location or minimal distance between sensors and different shaped or sized object or subject signals of interest. For the MEG example embodiment a i) multi-helmet Dewar system (i.e. plurality of Dewar sensor system interfaces (i.e. helmets) enabling (for example) in the case of MEG imaging or monitoring of adults or children based on selecting the appropriate sized sensor system helmet (i.e. paediatric or adult) by means of horizontal Dewar rotation (see also FIG. 2 to FIG. 10 and descriptions).

The invention provides a magnetic monitoring system or MMS for imaging, monitoring, scanning or mapping for brain or heart activity of subjects including children and adults, the system comprising of a magnetoencephalographic or magnetocardiographic system incorporating SQUID sensors for brain activity and heart activity; a plurality of Dewar helmets of variable sizes and shapes; and a plurality of monitoring interfaces; wherein the sensor system helmet is moveable by horizontal Dewar rotation. The MMS may further comprising of meaning for multi-functional MMS selectable or reconfigurable sensor (i.e. helmet) system. The MMS Dewar helmets most advantageously may be of different sizes and shapes. The MMS may include a three-dimensional sensor system positioning adjustment capability for optimal spatial resolution, signal sensitivity, and/or enhanced multi-modal image co-registration precision. The MMS may have the three-dimensional sensor system positioned automatically or manually. The MMS may include a shared or common coolant system including single reliquification coolant system. The MMS may include means for simultaneous electroencephalographic monitoring capabilities. The MMS may include precision co-registration fiducial options. The MMS may include a Double Relaxation Oscillator SQUID (DROS) system with close coupled SQUID chip and coil, enabling high flux to voltage sensitivity. The MMS of claim 9, wherein the close coupled SQUID chip and coil is configured for maximal flux to voltage sensitivity, thereby minimizing the stray pickup noise and impedance (resistance; inductance; capacitance) by way of virtual direct coupling between SQUID amplification chips and corresponding pick-up coils. The MMS may include capabilities localization (i.e. selection and positioning of Dewars fitted with radio frequency therapy and/or Dewars and/or RF beams to be positioned optimally) in terms of neural sources to be avoided in radio frequency targeting or beam-shaping or regions to be targeted for removal or mitigation of cancer cell risk.

Most advantageously, the system may incorporate a vacuum cooled sensory system, with very low-vibration enabling continuous coolant operation, even during coolant recovery or recycling phases, due to sealed and vacuum chamber separation of sensitive SQUID and other sensor components. The system may also include an automatic level adjusting Dewar coolant system, including 3-D repositioning super-conducting coolant operability (regardless of gravity, tilt and other Dewar repositioning). The system may also include 3 D subject scanning and/or pre-scanning means to determine optimal 3-D sensor position co-ordinates and associated optimal positioning control. The system may include Dewar positioning safety sensor and/or sensor systems located on and around the Dewar and other moving components so that collision with subjects or others in vicinity of the MMS is avoided at all times and under all conditions, including adjustment or repositioning of the Dewar.

DETAILED DESCRIPTION OF THE INVENTION

The invention provides the following features with reference to the Figures. It will be understood that the invention is limited only by the claims appended hereto.

FIG. 1 shows an embodiment showing MMS multi-helmet Dewar system with x-axis (4; horizontal rotation) and/or y-axis (5; vertical height) and/or z-axis (6; angular tilt) manual or automatic positioning system (3D positioning system or X/Y/Z auto-positioning system) as well as a unique vacuum radiation cooled senor system (10) designed for very low-vibration during super-conductive cooling conditions of the sensory system, and/or;

With respect to the Blocks in FIG. 1, the following is described. Block 1. Dewar adjustment mechanism cabinet.

Blocks 2. & 9. Multiple light-beam and/or RF and/or ultrasonic transceiver systems located within the magnetic shielded room (or external area simulating the subject positioning of the magnetic shielded room), enabling subject to be scanned, whilst in ideal monitoring position, typically prior to MMS investigation to allow exact region of subject of interest (i.e. head scan) to be captured in an accurate 3-dimensional (3-D) co-ordinate format, for MMS system operator validation and adjustment is required, followed by option of storing subject's body, limb and head outline details, so that the MMS system can then compute the optimal 3-Dimensional position of the Dewar in order to provide the best image and monitoring capabilities, whilst ensuring a safe space is established between the subject and the MMS. In this manner the present invention's MMS automatic horizontal rotation selection (i.e. as part of the present invention's multi-sensor Dewar system can be selected in accordance to Dewar that best matches shape and size of subject's monitored region (i.e. adult or paediatric head, in this example embodiment), as well as ideal vertical height position (to accommodate standing, lying or seating position or size of bed or seat etc.), as well as ideal tilt angle (i.e. accommodate seating or lying or other positions).

The scanned subject outline co-ordinates can then be referenced in order to determine the corresponding optimal Dewar 3-Dimensional Dewar positioning.

Additionally, precise electrode positions can be accessed via available data or derived via scanning (RF or light beam) subject with electrode and/or associated fiducial markers.

Various combinations of MMS Dewar 3-D positioning and subject pre-scanned 3-D data can be stored and recalled as part of a library of test montages. This data can be transferred directly for Dewar manual or automatic x and y and/or z axis configuration. This Dewar adjustment can occur when subject is in magnetic shielded room or otherwise at a separate time, as required in terms of regulatory, safety and other important conditions.

Block 3. Dewar adjustment cabinet interface electric, electronic, fibre-optic and/or hydraulic interface for remote location of Dewar x, y and/or z axis positioning system Block 4. Dewar horizontal rotate system.

Block 5. Dewar vertical height adjust telescopic rod and sleeve using adjustment cog and slot.

Block 6. Dewar vertical pivot/tilt joint.

Block 7. Insulation Space

Block 8. Vertical Dewar rotation telescopic rod and sleeve with tilt rotate joint using clamp bracket mechanism, can be fitted to the outside of the "helium fill" chamber adjustment cog and slot.

Block 10. Coils, Bobbins, SQUIDS in Vacuum Space

Block 11. Simple, stream-lined, minimalistic design with no infrastructure support columns required within helium reservoir which can move with vibration in liquid helium.

Figure 2:
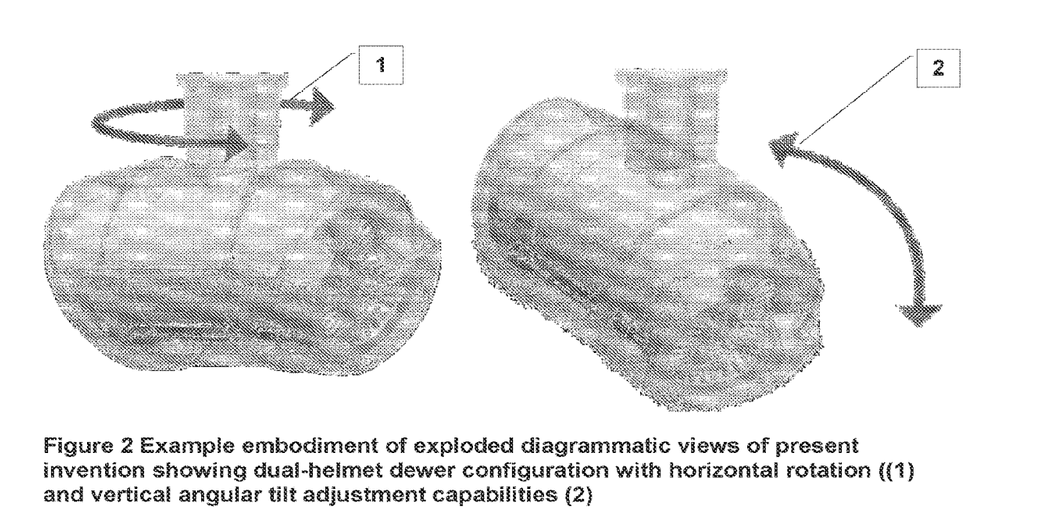
FIG. 2 shows an embodiment of exploded diagrammatic views of present invention showing dual-helmet dewer configuration with horizontal rotation ((1) and vertical angular tilt adjustment capabilities FIG. 3 shows exploded diagrammatic views of an example of the dual-Dewar function, incorporating vertical height adjustment capability, enabling accommodation or different bed, seat, standing or other subject variable imaging and/or monitoring requirements.
Figure 3:
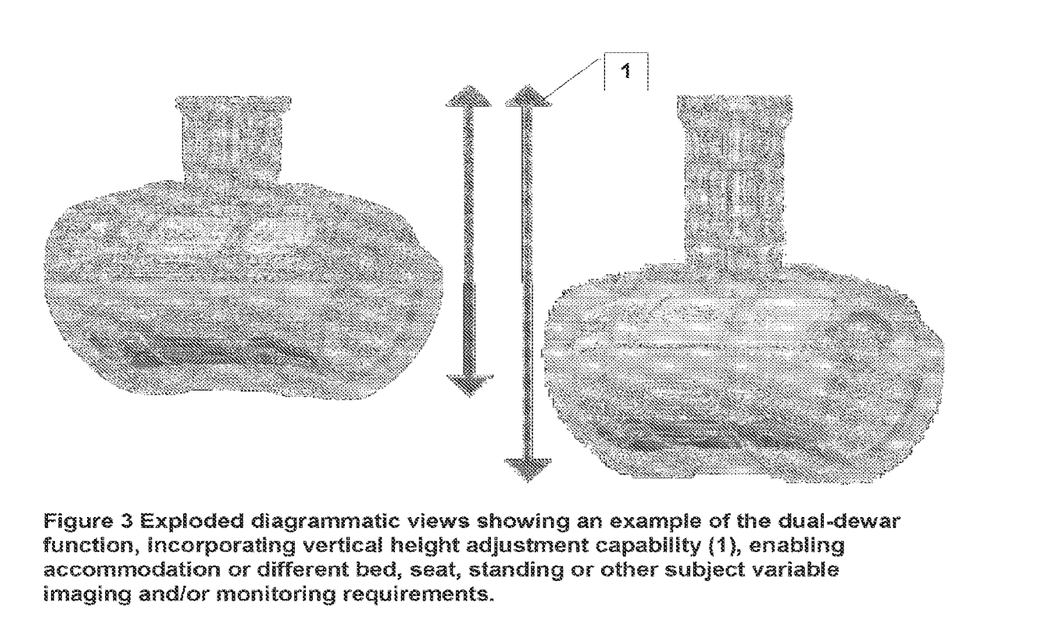

FIG. 2.

Left exploded diagrammatic view showing an example of dual-Dewar function incorporating 180 degree horizontal rotational capability in left drawing, allowing selecting between one or more Dewar and helmet head shapes or sized arrangements (such as child or adult configurations).

Block 1. MMS (MEG version) example embodiment of 180 degree rotation for paediatric and adult Dewar usage capability.

Block 2. MMS (MEG version) of tilt angular positioning adjustment enabling subject to be seated, lying, standing or positioned in any other intermediate positions during MMS investigations.

Right exploded diagrammatic view showing an example of dual-Dewar function incorporating vertical tilt capability for adjustment with seating, supine or any range of sloped or other subject positions, enabling imaging and/or monitoring to be conducted, for example, during any number of physical positions such as rest, sleep, wake, unconsciousness and other psychological and physical states.

The present invention example embodiment, as shown here provides a means of flipping or rotating the dual-Dewar system around to select the most appropriate Dewar for the subject under MEG investigation.

Typically the dual-Dewar format can be configured to accommodate 2 adults, 2 paediatrics or one adult and one paediatric.

To minimise space or overall MEG facility footprint (area required for MEG operation) and cost requirements, whilst maximise the system usage capabilities, a dual-Dewar systems can be deployed, whereby the system is configured in a single small magnetic shielded room, thereby only accommodating room for one MEG investigational subject at any one time.

Alternatively, in other configurations a larger magnetic shielded room can be deployed with a more comprehensive system configuration (allowing both Dewars to be operated simultaneously, whereby two complete sets of electronics are deployed to process all SQUID signals from both Dewars simultaneously. In such a configuration the magnetic shielded room would be of adequate size to allow subjects to be investigated from each of the two Dewars at one time or separate times, as required. A visual barrier and if required additional magnetic shielded barrier could be configured to separate the two Dewar and MEG subject imaging and monitoring areas.

A key advantage of the dual-Dewar system is to enable the provision for two separate optimally sized MEG helmets. This is particularly important as the sensitivity and subsequent signal to noise of the MMS/MEG/MCG system is greatly enhanced by minimising the space between the head (or other region) of the subject being imaged and monitored and the SQUID sensor coils. Therefore having a larger head sized helmet and SQUID system contained as part of one Dewar (i.e. adult sized) and a smaller (i.e. paediatric sized) monitoring configuration as part of the second Dewar provides improved data quality, with optimal sensitivity, based on the subject/object demographics, when compared to utilising one general sized Dewar for the larger and smaller head sizes. In prior art systems it was often necessary, during MEG investigations, to image and monitor one hemisphere of a child's brain (i.e. by leaning the child towards one side of the Dewar helmet) and then separately image and monitor the other hemisphere of a child's brain (i.e. by leaning the child towards the other side of the Dewar helmet). The two separate MEG scans would then need to be combined, which of course added further errors and complexity to the MEG process.

FIG. 3.

Block 1. Example of vertical MMS (MEG Dewar in this example) height adjustment capability.

Figure 4:
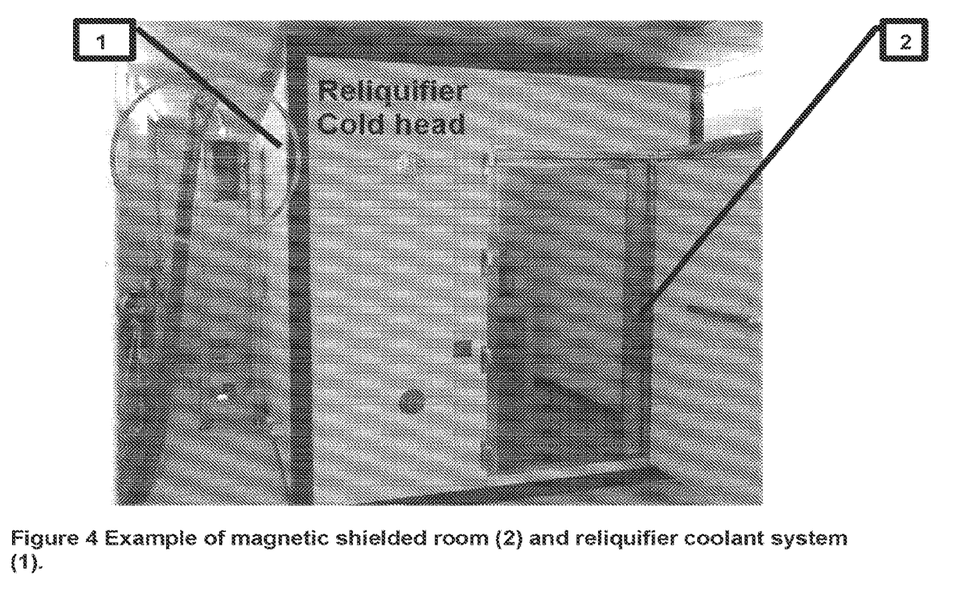
FIG. 4 shows an example of a magnetic shielded room and reliquifier coolant system.

FIG. 4.

Block 1: MMS/MEG/MCG/Subject typical magnetic shielded room (1) isolating external noise and interference so that magnetic signals from a subjects head can be imaged and monitored, even when such signals are about 1 billionth the size of the earths normal magnetic field. Coolant reliquifier system (2).

Block 2: Integrated zero-loss helium recycling reliquifier system, enabling virtual vibration-free continuous operation helium reliquification system integrated into the present invention MMS (MEG format in this example embodiment), thereby also greatly reducing operational and maintenance costs.

Figure 5:
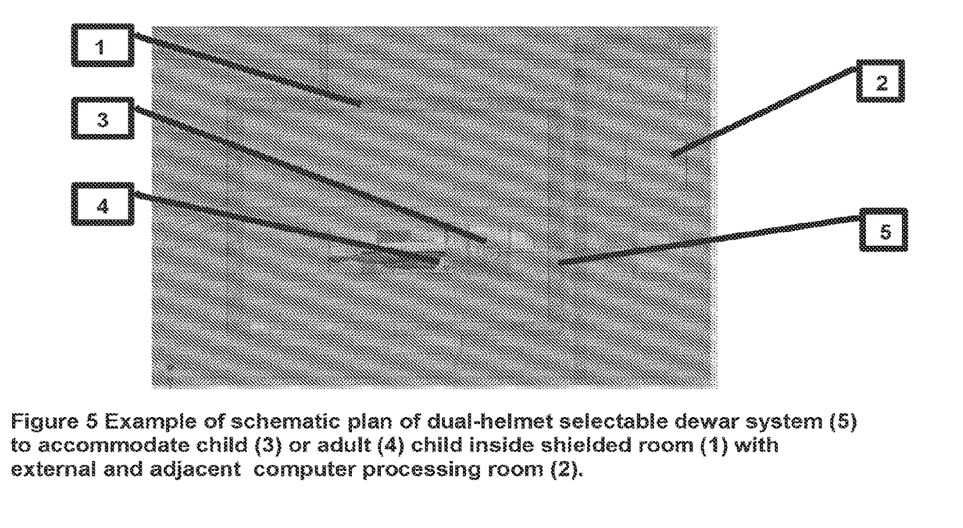
FIG. 5 shows an example of schematic plan of dual-helmet selectable Dewar system (5) to accommodate child or adult child inside shielded room with external and adjacent computer processing room.

FIG. 5.

Schematic of Dual-Dewar system (5) demonstrating the ability of the dual-Dewar MMS/MEG/MCG/Subject system incorporate a smaller magnetic shielded room (1), using the horizontal selection (Dewar flip/rotate) function, as shown here.

The subject in this schematic representation shows dual usage of system with paediatrics (3) or adults (4), using dual 180 degree rotation Dewar selection function. The subject is shown lying in supine position.

The left square room is the magnetic shielded room, whilst the right of drawing section shows the computer, cognition test control and image viewing room (2).

FIG. 6.

Exploded diagrammatic view showing example of dual-Dewar with selection of child imaging and/or monitoring configuration during seated subject position. The picture shows the Dewar tilted at an angle of about 45 degrees off horizontal axis (1) to accommodate seating position, whilst the Sensing system optimised for shape and size for child (2) investigational purposes.

FIG. 7.

Example of dual-Dewar with selection of adult supine positioned imaging and/or monitoring configuration. The picture shows the Dewar at the horizontal position without tilt (1) to accommodate supine lying position of adult subject (2), in this example. This example embodiment of the present invention shows the adult Dewar sensor system (3) being deployed (versus the paediatric sensor system on the other side of dual-Dewar; Block 1), whereby this adult MMS (MEG) Dewar selection and usage deploys the optimal sensory system and helmet shape and size, thus minimising the space between the sensitive sensors and the subject's brain signals of interest.

Figure 8:
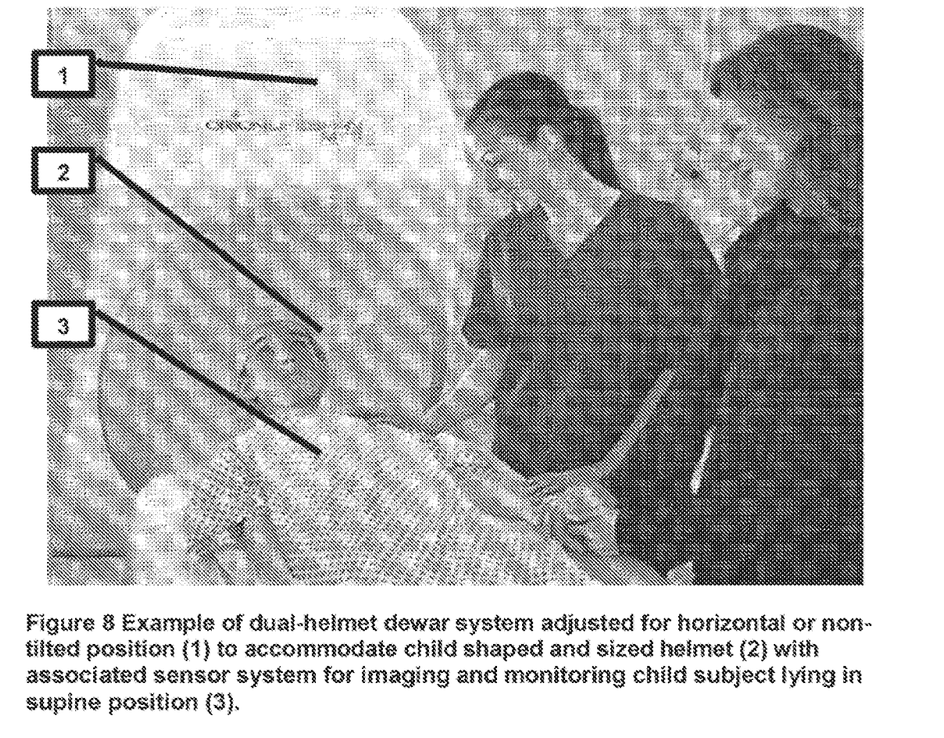
FIG. 8 shows an example of a dual-helmet Dewar system adjusted for horizontal or non-tilted position (1) to accommodate child shaped and sized helmet with associated sensor system for imaging and monitoring child subject lying in supine position.

FIG. 8.

Example of dual-Dewar (1) with selection of child imaging and/or monitoring configuration for minimal space between child's brain signals and sensory system (2) to achieve maximum signal to noise MMS quality) during supine subject position (3). A plastic helmet-shaped insert (2) safely separates and insulates (electrically and temperature-wise) the MMS (MEG in this example embodiment) from the super-cooled sensor system from the child. This example embodiment of the present invention shows the paediatric/child Dewar sensor system (2) being deployed (versus the adult sensor system on the other side of the dual-Dewar; Block 1), whereby this paediatric/child MMS (MEG) Dewar selection and usage deploys the optimal sensory system and helmet shape and size, thus minimising the space between the sensitive sensors and the subject's brain signals of interest.

FIG. 9.

Figure 10:
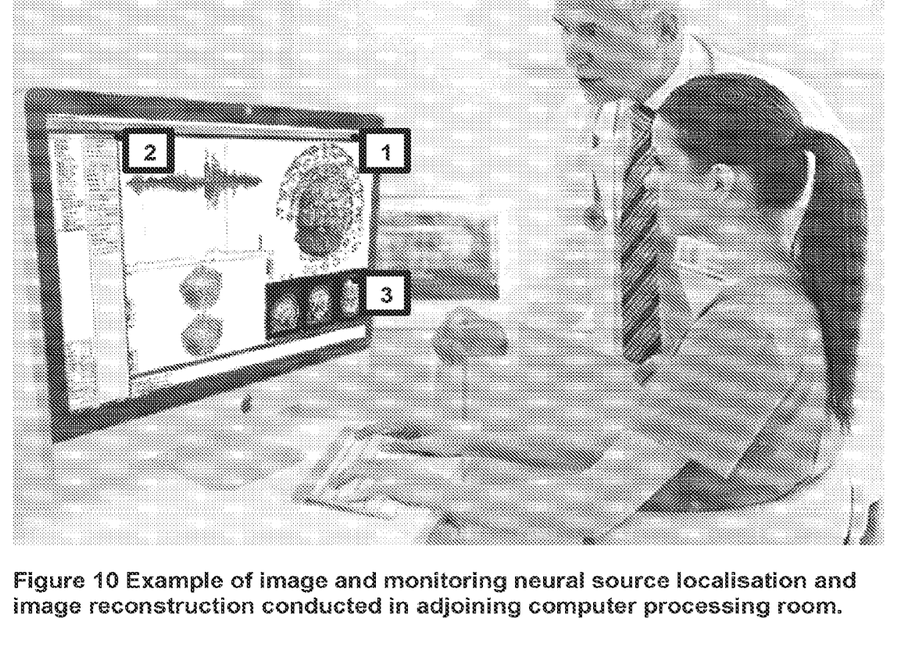
FIG. 10 shows an example of image and monitoring neural source localisation and image reconstruction conducted in adjoining computer processing room.

Unique dual-helmet (dual-Dewar) rotating (1) adult/paediatric Dewar system with shred coolant entry and feed system (2) and unique sensor system (3) (shown via exploded view in this diagram) surrounded by a vacuum seal compartment able to the cooled for super-conductive SQUID requirements using radiation principles, thereby isolating the very sensitive SQUID chips, bobbins and associated pick-up coils from excessive vibration noise and other problems associated with the coolant flowing or interacting directly with these said sensitive sensor system components;

FIG. 10.

Integrated reference fiducial markers with multi-modality imaging and/or monitoring capability enables precision convergence capability, calibration and verification, thereby improving determination of combined or discreet combinations of surgical output visualisations and co-ordinates for surgical or cancer treatment guidance during, pre and post-operative, with options of actual or simulated surgical or cancer treatment synchronised views. The upper right hand computer monitor view is a 2D representation of a 3D (3D viewing capabilities are possible) head with the ability for the EEG electrodes to be visualised (1) and also for the MEG scanner to automatically scan via any combination of video radiofrequency or light beams the actual and precise position of each EEG electrode during imaging as well as the precise locational measurement centres of the MEG reference coils (by way of touch or RF or light beam or ultrasound touch sensors providing positional information of the subjects head and/or EEG sensors and/or additional; subject—located fiducial convergence alignment sensors or locators). Other modalities such as CAT, CT, PET, MRI (3), near field infrared imaging can be overlayed using cross-compatible physical or image computed image and/or monitoring convergence fiducial alignment sensors or markers or locators).

The top left of computer display presents a time segment of EEG data capable of being time-synchronised and spatially aligned with right hand computer screen image (2).

The lower right computer screen image represents the scanned image (2) used as part of the real boundary element modelling determination in order to enhance the accuracy of neural source localisation, which can be overlayed and/or time synchronised and/or or superimposed in the lower left and lower right computer screen views.

The present invention includes improved Dewar components, functions and methods for MMS including MEG systems, and thereby enable greater range and flexibility to accommodate positioning closer proximity imaging and monitoring to the bodies of a broad range of subjects, the present invention further comprising any of:

ii) Multifunctional MMS selectable or reconfigurable sensor (i.e. helmet) system, and/or;

The present invention includes the provision for any number of Dewars with any number of sensor interfaces (including helmets in the case of MEG imaging) or other subject/object measurement interfaces.

The present invention includes the provision for a multiple-rotor selectable MMS Dewar, whereby any number of subject/object interfaces can be deployed to accommodate a range of different subject/object sizes and positions for imaging or monitoring.

iii) 3-dimensional (3-D) sensor system positioning adjustment capability for optimal spatial resolution, signal sensitivity, and/or enhanced multi-modal image co-registration precision along with associated descriptions.

iv) 3-D manual or automatic Dewar and/or sensor system positioning or reconfiguration system, and/or;

v) shared or common coolant system including single reliquification coolant system, block 11) enabling thermal radiation (i.e. from coolant reservoir block 11) to adjacent but separately vacuum sealed and radiation super-conductive operation cooled sensor chamber(s); block 11)) to a plurality of sensory systems (block 10 and associated descriptions), and/or;

vi) shared or common coolant feed and/or return system, including 3-D movement positioning flexibility (block 4, 5 and 6, along with associated descriptions), and/or;

vii) vacuum cooled sensory system, with very low-vibration enabling continuous coolant operation per block 10, showing coolant reservoir and separation of vacuum sealed sensor chambers per block 10, along with associated descriptions (see block 1 reliquifier coolant system and associated descriptions), and/or;

viii) automatic level adjusting Dewar coolant system, including 3-D repositioning super-conducting coolant operability (regardless of gravity, tilt and other Dewar block 4, 6 and 6, along with associated descriptions, and/or;

ix) 3D subject scanning and/or pre-scanning system to determine optimal 3-D sensor position co-ordinates and associated optimal positioning control (block 2 and 2, along with associated descriptions), and/or;

x) simultaneous EEG or other imaging or monitoring modality capabilities including precision co-registration fiducial options, and/or;

xi) Double Relaxation Oscillator SQUID (DROS) system with close coupled SQUID chip and coil, enabling high flux to voltage sensitivity, and/or;

xii) close coupled SQUID chip and coil for maximal flux to voltage sensitivity, and/or;

xiii) whereby MMS therapy capabilities include localization (i.e. selection and positioning of Dewars fitted with radio frequency (RF) therapy and/or Dewars and/or RF beams to be positioned optimally) in terms of neural sources to be avoided (i.e. healthy cells) in radio frequency targeting or beam-shaping or regions to be targeted for removal or mitigation of cancer cell risk; and/or ix) Dewar positioning safety sensor and/or control system.

The present invention includes a Magnetic Sensing (MMS refers to imaging and/or monitoring and/or scanning and/or mapping system, including any of: Magnetoencephalography (MEG) and/or Magnetocardiography (MCG)) system incorporating multiple MMS Dewar-interface (Dewar-subject/object-interface, such as helmet or other head, body or limb Dewar-interface) shapes or sizes, in order to accommodate optimal MMS sensing (including SQUIDS) by way of minimising locational proximities for different groups of subjects or objects (I.e. head, body, limb) sizes or shapes, applicable (I.e. but not limited) to different age groups such as paediatrics (Infants—a child of up to 12 months of age; Child~1 to 12 years; Adolescent~13 to 16 years) and/or adults, the present invention further comprising of any of (i) to xiii):

i) two or more sensor systems and associated helmets are arranged into a single Dewar, whereby the desired sensor system (i.e. preferred shape or size) to image or monitor subject of interest, can be selected via horizontal rotation of Dewar system until selected sensory system is located at required subject investigation position, and/or;

Plurality of helmet sensor system interfaces whereby the said MMS system incorporate a plurality of MMS Dewar-interfaces (such as but not limited to MCG body-interfaces and/or MEG helmets, which presents an example embodiment of multiple helmets and associated Dewars, along with corresponding magnetic sensor configurations (i.e. SQUID arrays per Block 10), and/or;

Whereby, and as reference to "helmet" suggests, this relates to Dewar-interface for MEG head sensing but word helmet can be substituted for Dewar-interface which covers other biological or objects under investigation, and/or;

ii) Multifunctional MMS selectable or reconfigurable sensor (i.e. helmet) system, including capability to rotate Dewar in accordance to selected sensor system, whereby dual Dewar system allows (for example, only) 180 degree horizontal rotation between selection of adult or paediatric sensor system. In the case of a three sensor system Dewar the Dewar can be rotate at 120 degree intervals for the required selection of any of 3 sensor shapes and size types. Similarly, the formula applied to determine the rotational activation for selecting each successive sensor system can be represented by the following: number of sensory systems divided by 360 degrees.

The said MMS incorporates a multifunctional selectable multi-sensor system, whereby MEG helmets or other magnetic sensing formats can be reconfigured to suit subject under diagnostic or therapeutic investigation (i.e. cancer or radiofrequency beam shaping and/or targeting capabilities), and/or;

the said MMS system incorporating a plurality of MEG helmets or other types of MMS Dewar-interfaces corresponding to one or more MMS Dewars, whereby in some configurations multiple helmets or other Dewar interface with any combination of one or more Dewars can be enabled. Similarly, the formula applied to determine the rotational activation for selecting each successive sensor system can be represented by the following: number of sensory systems divided by 360 degrees, and/or;

The said MMS incorporating a plurality of sensor interfaces, such as MEG helmets or other magnetic sensing interfaces (including within one of more Dewars), thereby enabling the Dewar sensor-interfaces (i.e. helmet) to accommodate imaging and/or monitoring a range of different head shapes and sizes of subject/object with minimal distance between sensor system and brain signals of subject/object under investigation, and/or;

the said MSS system incorporating a plurality of MEG Helmets or other types of MSS Dewar interfaces (including but not limited to MEG or Magnetocardiography (MCG) Dewar interfaces, thereby enabling selection or re-configuration of optimal MSS Imaging/monitoring proximity localisation corresponding to investigation and/or therapy, applicable to a range of object or subject sizes and/or shapes, in accordance to different magnetic sensor configurations (i.e. types or formats or sizes or techniques or number of monitored or imaged channels etc.) for subject(s) or object(s) of interest, and/or;

whereby MMS therapy capabilities include localization of neural sources to be avoided (i.e. healthy cells) in radio frequency targeting or beam-shaping or to be targeted for removal or mitigation of cancer cell risk; and/or whereby MMS configuration can be deployed in a manner enabling one or more objects or subjects to be imaged or monitored at any time, and/or whereby MMS configuration can be deployed in a manner where a single object or subject can be imaged or monitored at any one time, thus reducing on magnetic shielded room size or other requirements, and/or;

iii) 3-DIMENSIONAL SENSOR POSITIONING SYSTEM: In one embodiment the present invention incorporates any combination of tilt, horizontal rotate (i.e. enabling multi-sensor Dewar capability) and/or vertical height adjustment; and/or;

the said MMS incorporating multiple sensor-systems (such as multiple helmets in case of MEG deployment example of MMS), enabling a plurality of different head sizes and shapes to be accommodated, whilst minimizing the distance between brain signal activity of interest and corresponding sensor system;

the capability for said MMS system (including option of MEG sensor helmets) to enable horizontal rotation (i.e. 180 degrees in case where 2 MEG sensor helmets (or other MMS Dewar-interfaces) are used or 120 degrees in case where 3 MEG sensor helmets (or other MMS Dewar-interfaces) are used or 90 degrees in case where 4 MEG sensor helmets (or other MMS Dewar-interfaces) are used and so on—i.e. 360 degrees divided by number of different Dewar-interfaces deployed equals rotational increment associated with selection of each different Dewar-interface, and/or;

the MMS system further incorporating the capability for vertical angular tilt adjustment of helmet (or other sensor interface) to accommodate a range of subject positions such as seated or supine subject imaging and/or monitoring positions, and/or;

The present invention further enables adjustable vertical tit of Dewar and/or Dewar interface, to accommodate a range of subject/object shapes and sizes or positions for imaging or monitoring, and/or capability for said MEG sensor helmet able to be vertically repositioned (I.e. Pivoted through 90 degree positional adjustment arc) in order to accommodate a range of subject positions including supine or seated upright or any intermediate positions, and/or;

whereby MMS configuration can be deployed in a manner where noise reduction techniques can be incorporated in order to minimise or avoid magnetic shielded room requirements, and/or;

whereby selection or rotation of Dewars and/or Dewar-interfaces can be deployed in a manual or automatic manner, and/or;

The MMS incorporates 3-D Dewar spatial parametric adjustment positioning capability enabling any combination of tilt, horizontal rotate and vertical height adjustment, and/or;

iv) the present invention enables any combination of automatic or manual multi-sensor Dewar positioning options (for MMS system, including MEG or MCG or other subject or object imaging and monitoring formats) in order to configure MMS Dewar system for the required vertical height (x-axis adjustment), the selected helmet sensor system (horizontal rotation of Dewar (Block 1) or the angular tilt of the Dewar helmet (block 2) in accordance to the respective height and posture (i.e. age, sitting, standing, lying, along with any other positions), according to selecting the most appropriate helmet shape and size (i.e. head shape and size and whether subject is an adult or paediatric), and in accordance to the optimal angular tilt, based on whether subject under investigation, and/or;

As it relates to manual or automatic horizontal rotation adjustment capability, in one embodiment example a "vertical Dewar rotation telescopic rod and sleeve", using clamp bracket mechanism, can be fitted to the outside of the "helium fill" chamber (see FIG. 3) in a manner where using an arrangement of cogs and connection rods or chains interacting with the "vertical Dewar rotation telescopic rod and sleeve" in a manner where a manual wheel adjustment or automatic computer controlled motor servo adjustment can horizontally rotate the Dewar to and desired position across a 360 degree range of rotational positions. I.e. A cog positioned around the outer circumference of the "vertical Dewar rotation rod and sleeve mechanism" can interact with another cog, which is fixed to the "Dewar ceiling mount bracket" support system in a manner where a manually driven or automatic service driven cog, attached to the fixed platform of the stationary part of the "Dewar ceiling mount bracket" support system (versus "vertical Dewar rotation telescopic rod and sleeve mechanism" which rotates in accordance to desired Dewar rotational selection) can rotate the "vertical Dewar rotation telescopic rod and sleeve mechanism" as selected by system operator, and/or;

As it relates to manual or automatic vertical rotation or tilting adjustment capability, in one embodiment the said "vertical Dewar rotation telescopic rod and sleeve" can incorporate a flexible joint, whereby the said "rod and sleeve" arrangement resides in the upper arm of the said join, so that the lower join arm can be rotated in respect to the upper joint arm across a range from 0 degrees (Dewar in horizontal untitled position) to plus or minus about 90 degrees, via a series of manual or automatically driven cogs and/or drive chains or belts to rotational position required. i.e. a screw thread adjustment arm arrangement whereby the upper arm's (above swivel joint block 3) inner core or adjustable outer sleeve can interconnected via a screw threaded bar to the lower arm (below swivel joint block 3) via a matching screw, so that the upper threaded screw can be screwed clock-wise or anti-clockwise to lift or lower the lower arm with respect to the upper arm, in order to change the angular tile of the Dewar system, and/or;

As it relates to manual or automatic horizontal Dewar height adjustment, capability, in one embodiment example the said "vertical Dewar rotation telescopic rod" (upper arm of vertical tilt joint) can incorporate a sleeved rod arrangement telescopic adjustment arrangement, whereby the inner rod has precision ratchet impressions located in a the upper vertical tilt arm and the outer sleeve contains a manually or automatically driven cog arrangement that, via a slot window in the outer sleeve, allows the inner rod and outer sleeve to be extended and contracted in accordance to the system users desired Dewar height adjustment, and/or;

The Dewar horizontal rotation, vertical height and pivot or tilt adjustments can be contained within "Dewar adjustment mechanism" (shown here in the upper section of the "helium fill" chamber. Mechanical couple rods and coupling mechanism can be attached via bracket and manual adjustment kit to the "Dewar adjustment mechanism" cabinet, enabling manual adjustments to be accessed conveniently by system operator or technician. The Dewar movement and adjustment mechanisms can be covered by external system covers to enhance system industrial design aesthetics and system operation eloquence, aesthetics and also improve system operational safety. In this manner the system can be configured or automatically (I.e. via a range of preprogrammed or screen display options) or manually adjusted, as required, and/or;

Additionally, the present invention can deployed using a combination of mechanical screw adjustment systems and/or hydraulic positioning systems, as commonly used in aeronautics design for the movement of tail-rudders, wing flaps and other mechanical adjustment systems Similar to fundamental aeronautics design principles, the present invention can be controlled by wire (i.e. as most modern planes are flown by wire), whereby computer servo positioning and remote wire and/or wireless interconnection provide the control and/or drive signals required to undertake mechanical Dewar horizontal rotation, vertical height adjustment or tilt angular adjustments in a 3-dimensional (x and/or y and/or z-axis of movement). Orion LifeSpan Multi-Dewar (example shows dual-helmet MEG squid sensor system), and/or;

v) A single shared or common Helium Reliquification system (see Block 1) is enabled by way of sharing a common helium coolant reservoir by a plurality of Dewars (dual-helmet sensor system in this example embodiment, Block 11). The single coolant reservoir includes associated filling and return feed coolant gas isolated for vibration via flexible piping to the cooling head mount, located outside the MSR (i.e. via access with top central round pipe (Block 12) feeding into a central (between 2 sensory systems located in separate vacuum spaces) helium reservoir section (Block 11), and/or;

the MMS incorporates a shared or combined multi-helmet Dewar reliquifier coolant reservoir capable of being deployed for super-conduction sensor system operation across a plurality of MMS sensor systems, and/or;

vi) common or shared (between a plurality of sensor systems) coolant liquid (I.e. Helium) feed and coolant gas return hoses (or pipes or ducts), interconnected between the top of the "helium fill" chamber (as shown in FIG. 3) and the reliquifier coolant unit (located outside the magnetic shielded room as shown in can be arranged in a manner whereby additional free hose flexibility allows the Dewar unit (dual in this example but any multi-Dewar format can be enabled) to be:—lifted or lowered (to accommodate different vertical height positions of subject under investigation) and/or;

vertically pivoted or tilted to enable different Dewar horizontal angles, thereby accommodating MMS/MEG/MCG sensory system to be optimally adjusted for ideal close proximity and ideally localised sensor MMS/MEG/MCG/SUBJECT system usage (i.e. minimising distance between sensing system and the signals of interest of the subject under investigation) during various positions of subject under investigation. i.e. Dewar adjusted for horizontal position with subject in supine position or angled downwards (from 0 degree horizontal axis) by 45 degrees (per seated subject example, and/or;—horizontally rotated to select appropriate Dewar for subject of investigational interest. i.e. 180 degree rotation capability to select between adult or paediatric Dewar and sensor system for the example in this FIG. 3, and/or;

vii) One or more vacuum cooled sensory systems partitioned adjacent to helium reservoir to enable cool temperature via radiation, (versus noisier and more vibration-prone direct thermal conduction or thermal convection cooling reliance), with physically separated thermal radiation cooled sensor system (i.e. avoid direct contact coolant and sensor system in order to minimise vibration and other noise created with coolant flowing over sensitive sensor system components), and/or;

the MMS incorporates a vacuum space around the sensor systems), thereby enabling radiation cooling, with coolant reservoir containing coolant fluid or gas, Block 11) to be separated from sensor system(s) (Block 10) in order to minimise noise and vibration and other interference, by way of deploying coolant radiation versus need to apply direct contact coolant and/or coolant conductance method and/or or coolant conventional method, and/or;

whereby the coolant system's gas or liquid does not need to flow directly around the sensitive sensor system components. In this example the MEG sensor system semiconductor SQUID chips, SQUID pick-up coils, pick-up coil bobbins per Block 10. This approach is also applicable to MCG, as well as imaging or monitoring other object, body, limb, subject parts. Additionally, this vacuum separation (between coolant and sensor systems) and radiation cooling technique can be applied to sensitive sensor (vibration and other noise sensitive) components of MM; PET; CT. CAT, X-ray, ultrasound imaging or monitoring systems, and/or;

whereby coolant gas/liquid is isolated from the low-noise but super cooled vacuum sensor system region of the MMS—the sensor system is cooled via radiation versus direct coupling temperature convection or conduction approaches, thereby minimising noise and vibration otherwise induce via coolant flowing directly over sensitive sensor components; and/or;

whereby vacuum radiation cooled sensor system can be deployed: The unique combination of the vacuum cooling system, and the multi-sensor Dewar (i.e. in this example: multi-helmet Dewar system), coupled with the single shared helium (or other coolant composition) reliquifier coolant system (Block 1) and coolant reservoir (Block 11) delivering around 4 Kelvin temperature or minus 269 degrees Celsius required to maintain the sensor system super-conducting conditions (temperature required to activate low impedance electrical circuit superconducting state for SQUID amplifiers and coils) enables a very low-noise and low-vibration configuration so that helium recycling can be continuous, allowing 24/7 (continuous or uninterrupted) operation of the said MMS (I.e. no need to turn off coolant system during MMS Imaging or monitoring). In contrast, traditional earlier art systems require the coolant solution/gas to be switched off during critical scanning, due to excessive vibrational and other (i.e. impedance variations across (Block 12) sensitive circuits and pick-up coils) noise generated when the coolant flows directly over the most sensitive imaging and monitoring parts (including Coils, Bobbins, SQUIDs which can be located in the Vacuum Space, formed around these sensitive sensor system parts, Block 10). Additionally, the shared coolant system and separate vacuum cooled sensor system compartments (separation between Blocks 10 and 11) enables greater range of measurement capability (via two or more separate shaped and sized sensor systems), whilst also reducing maintenance costs associated due to the simpler system (compared to multiple cooling systems), or avoidance of corrosion or wear or related impedance variations, associated with coolant making direct contact with or flowing around sensitive sensor system parts (SQUIDs, coils, etc.). The use of the vacuum coolant system in the present invention reduces vibration and noise, which is otherwise more apparent in traditional MEG coolant system where direct coupling to SQUID coils and/or SQUID amplifiers create additional noise, such as vibration noise. Importantly, the vacuum coolant system requires no down time for Helium Return (i.e. helium return cycle does not discernibly increase imaging or monitoring system signal noise), and/or;

viii) multi-sensor Dewar system has sensors and control systems controlling Helium level and/or avoidance of helium flow or slushing effect so that the helium or other coolant is always appropriately covering (regardless of tile and gravity impact on flow levels) the sensitive sensor compartment wall (where compartment wall represents barrier between vacuum cooled sensory system and coolant) or sensor systems (where coolant directly flows over sensor system components). In this way the angular tilting or other Dewar movement or positioning never prevent the coolant from cooling sensor system in a manner that enables superconducting operational conditions (i.e. SQUID coils and chips need to operate at—269 degrees Celsius to achieve super-conduction capabilities). An automatic coolant level adjustment is enabled by way of sensing systems within Dewar and/or the sensor systems to ensure coolant fluid levels, regardless of adjustment or tilt of Dewar, enables correct coolant operation for super-conducting sensor system operational requirements at all times;

ix) A subject scanning and/or pre-scanning system, enabling precision co-registration between MMS sensor systems and/or subject investigational region/spatial area of interest and/or multi-modality co-registration precision, and/or;

Capability to pre-scan (light and/or radio frequency with or without associated marker points/measurement fiducials) patient inside magnetic shielded room or external to magnetic shielded room (i.e. calibrated co-registration of seating or patient gantry can enable precision scanning outside magnetic shielded room but 3-dimensional measures and associated output co-ordinates of subject's observational target (i.e. head; body; limb; object) shape and size characteristics to be computed via scanning system. In this way the resulting co-ordinates can be deployed by the present invention to allow automatic or manual positioning of the Dewar and associated sensory system in context of the most optimal x-axis (optimal sized Dewar rotational selection), y-axis (height) and z-axis (tilt) configuration for subject under investigation, and/or;

the said MMS incorporating a subject scanning capability, thereby enabling the determination of the optimal head shape and size Dewar interface selection (i.e. MEG helmet) as well as the optimal x-y-z positioning of the Dewar with sensor interface, to achieve the most precise and sensitive (i.e. minima distance between brain signals of interest and MEG sensors) imaging conditions, and/or;

the scanning of subject outline for purposes of determining optimal helmet shape and size selection as well as Dewar helmet positioning can be undertaken prior, before or during the MMS imaging and monitoring activation, and/or;

x) Similarly, in terms of scanning subject for simultaneous or separately recorded (electroencephalography) EEG signals the subject EEG electrode placements can be manually entered and/or, scanned and transferred to MMS system data in order to ensure precise, calibrated and specified co-registration of EEG and MMS image or monitoring data is achieved. The scanning of other modalities such as positron emission tomography (PET), computer aided tomography (CAT), X-rays, ultrasonic, RF treatment modalities, and/or proton treatment modalities can also be co-registered in this manner, and/or;

Whereby optimal sensory system adjustment or positioning refers to x-axis, y-axis and z-axis 3-dimensional spatial positing and Dewar selection (and/or sensor system and/or associated or subsequent data or signal processing or control systems) to enable multiple-Dewar or single Dewar system to be optimised for maximal subject safety and/or comfort and/or sensitivity imaging or monitoring of the sensory system. For one example MEG embodiment of the present MMS invention, the MEG head helmet is selected by way of scanning subject's head with light-beam, radio frequency (RF) and/or ultrasound or other subject/object scanning technique, in order to determine the exact shape, size and position of the subject/object under investigation (including head in case of MEG example) so that the multi-Dewar horizontal selection function determines which Dewar is most appropriate for the particular subject under investigation (this is determined by the Dewar which is larger than the subjects head but the closest fitting to minimise the space between the subjects brain signals of main interest and the Dewar "helmet".

Whereby the "helmet" refers to the concave helmet-shaped, or in other words a plastic head-shaped plastic receptacle, that sits closely around subject's head on the concave side, whilst the convex side of the helmet separates the very cold sensor system (QUID coils, bobbins and chips) from coming into contact with the subject's head, and/or;

On the convex side of the said helmet the SQUID sensory system and very cold components are located, in a manner where the helmet prevents subject under investigation from being exposed to super cool temperatures. It is also important that this said helmet is large enough to avoid pressure being applied to subject under=investigation's head but small enough and shaped closely to the subject's head to minimise the space between the sensory system and the monitored and measured brain signals, and/or;

xi) Double Relaxation Oscillator SQUID (DROS) system with close coupled SQUID chip and coil, enabling high flux to voltage sensitivity, and/or, xii) Dewar positioning safety sensor and/or control system, and/or;

the said MMS further incorporating a Dewar and/or Dewar-sensor interface (i.e. helmet) safety system to avoid Dewar movement during repositioning and other adjustment or movement circumstances from being able to harm subjects or system users, and/or the incorporation of a safety sensing system which detects any slight touching of a person (i.e. detects slight pressure or has sensors (i.e. light or pressure touch) capable of alarming or deactivating MMS movement to avoid any harm to a person, and/or;

the incorporation of a safety sensing system, enabling prevention and/or alert and/alarm during circumstances where people are in safe-isolation area suitable to prevent any risk of harm to any individuals during selection or reconfiguration associated with appropriate Dewar and/or Dewar-subject—interface, and/or;

xiii) whereby MMS therapy capabilities include localization (i.e. selection and positioning of Dewars fitted with radio frequency (RF) therapy and/or Dewars and/or RF beams to be positioned optimally) in terms of neural sources to be avoided (i.e. healthy cells) in radio frequency targeting or beam-shaping or regions to be targeted for removal or mitigation of cancer cell risk; and/or whereby MMS therapy capabilities include localization (i.e. selection and positioning of Dewars fitted with radio frequency (RF) therapy xiv) Close coupled SQUID chip and coil for maximal flux to voltage sensitivity; The unique axial radial, double-relaxation axial gradiometer sensing system, block 10, block 2; block 3) comprising of double relaxation bonding squid (DROS), incorporating reduced SQUIDs stray coil and associated wiring noise for enhanced high flux-to-voltage transfer capabilities as well as large modulation amplitude and high stability against offset drift conditions.

The invention claimed is:

1. A magnetic monitoring system comprising of: a magnetoencephalographic or magnetocardiographic or a body investigational system incorporating super-conducting quantum interference device (SQUID) sensors for brain activity or function;
   a plurality of Dewar helmets of variable sizes and shapes;
   a vertical Dewar rotation telescopic rod and sleeve;
   a plurality of monitoring interfaces;
   a helium fill chamber;
   a clamp bracket mechanism; and
   a multifunctional multi-sensor (MMS) incorporating a three-dimensional sensor system positioning adjustment capability for the plurality of Dewar Helmets for optimal spatial resolution, signal sensitivity, and enhanced multi-modal image co-registration precision;
   wherein the plurality of Dewar helmets is moveable by horizontal Dewar rotation, vertical adjustment or angular tilting,
   wherein the vertical Dewar rotation telescopic rod and sleeve uses the clamp bracket mechanism, and can be fitted to the outside of the helium fill chamber in a manner where an arrangement of cogs and connection rods or chains interacting with the vertical Dewar rotation telescopic rod and sleeve in a manner where a manual wheel adjustment or automatic computer controlled motor servo adjustment can horizontally rotate the Dewar helmets to a desired position across a 360 degree range of rotational positions is used, and
   wherein the vertical Dewar rotation telescopic rod and sleeve incorporates a flexible joint, an upper arm above the flexible joint, a lower arm below the flexible joint, an upper arm inner core, and an upper arm outer sleeve, whereby the rod and sleeve arrangement resides in the upper arm above the flexible joint, such that the lower joint arm below the flexible joint can be rotated with respect to the upper arm across a range from 0 degrees to plus or minus about 90 degrees, via a series of manual or automatically driven cogs and/or drive chains or belts to a rotational position required
   whereby the upper joint arm's inner core or the upper joint arm's adjustable outer sleeve is interconnected to the lower joint arm via a screw threaded bar, such that an upper threaded screw of the screw threaded bar can be screwed clock-wise or anti-clockwise to lift or lower the lower joint arm with respect to the upper arm in order to change an angle of the Dewar helmets,
   wherein the three-dimensional sensor system is positioned automatically,
   wherein the MMS incorporates multiple sensor-systems enabling a plurality of different head sizes and shapes to be accommodated,
   wherein the MMS incorporates the capability for vertical angular tilt adjustment of helmet or other sensor interface to accommodate a range of subject positions, and
   wherein the MMS incorporates 3-D Dewar spatial parametric adjustment positioning capability enabling any combination of tilt, horizontal rotation and vertical height adjustment.

2. The system of claim 1, wherein the multifunctional multi-sensor (MMS) is selectable or a is reconfigurable sensor.

3. The system of claim 1 further comprising a shared or common coolant system including single reliquification coolant system.

4. The system of claim 1, further comprising of simultaneous electroencephalographic monitoring capabilities unit.

5. The system of claim 4, further comprising precision co-registration fiducial options.

6. The system of claim 1, further comprising of a Double Relaxation Oscillator SQUID (DROS) system with closed-coupled SQUID chip and coil, enabling high flux to voltage sensitivity.

7. The system of claim 6, wherein the closed-coupled SQUID chip and coil is configured for maximal flux to voltage sensitivity, thereby minimizing stray pickup noise and impedance by way of virtual direct coupling between SQUID amplification chips and corresponding pick-up coils.

8. The system of claim 1 whereby the system capabilities include localization in terms of neural sources to be avoided in radio frequency targeting or beam-shaping or regions to be targeted for removal or mitigation of cancer cell risk.

9. The system of claim 1 whereby the system capabilities include one or more vacuum cooled sensory systems partitioned adjacent to coolant reservoir to enable cool temperature via radiation to minimise vibration and other noise by avoiding the need to have coolant flowing over sensitive sensor system components.

10. The system of claim 1 whereby the system capabilities include vacuum cooled sensory system enabling continuous coolant operation during coolant recovery or recycling phases, due to sealed and vacuum chamber separation of sensitive SQUID and other sensor components.

11. The system of claim 1 whereby the system capabilities include automatic level adjusting Dewar coolant system, including 3-D repositioning super-conducting coolant operability.

12. The system of claim 1 whereby the system capabilities include 3D subject scanning and/or pre-scanning system to determine optimal 3-D sensor position co-ordinates and associated optimal positioning control.

13. The system of claim 1 whereby the system capabilities include Dewar positioning safety sensor and/or sensor systems located on and around Dewar and other moving components so that collision with a subject or others is avoided at all times and under all conditions, including adjustment or repositioning of Dewar, or repositioning of the subjects under investigation.

* * * * *